(12) United States Patent
Hauan et al.

(10) Patent No.: US 7,223,366 B2
(45) Date of Patent: May 29, 2007

(54) MEMS MEMBRANE BASED SENSOR

(75) Inventors: Steinar Hauan, Pittsburgh, PA (US);
John J. Neumann, Jr., Pittsburgh, PA (US); Todd M. Przybycien, Pittsburgh, PA (US); Michael Bartkovsky, Peckville, PA (US); Kaigham J. Gabriel, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 177 days.

(21) Appl. No.: 10/702,709

(22) Filed: Nov. 6, 2003

(65) Prior Publication Data

US 2004/0197227 A1  Oct. 7, 2004

Related U.S. Application Data

(60) Provisional application No. 60/424,135, filed on Nov. 6, 2002.

(51) Int. Cl.
  *C12Q 1/68* (2006.01)
  *G01N 15/06* (2006.01)
  *G01N 33/00* (2006.01)
  *G01N 33/48* (2006.01)
  *G01N 35/00* (2006.01)

(52) U.S. Cl. .................... 422/68.1; 422/50; 422/82.01; 422/82.02; 422/82.05; 422/83; 436/43; 436/63; 436/149; 436/164

(58) Field of Classification Search ............. 422/50, 422/68.1, 82.01, 82.02, 82.05, 83, 98; 436/43, 436/63, 149, 164; 29/592, 592.1
See application file for complete search history.

(56) References Cited

U.S. PATENT DOCUMENTS

| | | | | |
|---|---|---|---|---|
| 5,056,362 A | * | 10/1991 | Ang et al. ............... | 73/204.26 |
| 5,914,507 A | * | 6/1999 | Polla et al. .................. | 257/254 |
| 6,016,686 A | * | 1/2000 | Thundat ...................... | 73/23.2 |
| 6,085,594 A | * | 7/2000 | Gutierrez et al. ............. | 73/704 |
| 6,312,959 B1 | * | 11/2001 | Datskos ....................... | 436/147 |
| 6,539,774 B1 | | 4/2003 | Zinck et al. | |
| 6,596,236 B2 | | 7/2003 | DiMeo, Jr. et al. | |
| 2003/0210799 A1 | * | 11/2003 | Gabriel et al. .............. | 381/173 |

OTHER PUBLICATIONS

Amy W. Wang, et al., A silicon-based ultrasonic immunoassay for detection of breast cancer antigens, Jun. 1998, pp. 13-21, vol. B49, No. 1-2, Elsevier, Switzerland.

(Continued)

*Primary Examiner*—Jill Warden
*Assistant Examiner*—Brian Sines
(74) *Attorney, Agent, or Firm*—Jones Day; Edward L. Pencoske

(57) ABSTRACT

A micro-electro-mechanical system (MEMS) device is described having a membrane which can be induced to resonate and the frequency of its resonance can be monitored. Chemical moieties can be attached to the membrane, and these moieties can be selected such that they have an affinity for molecules of interest, especially biological molecules of interest. When molecules of interest bind to the moieties they increase the mass of the membrane and thereby change the frequency of the membrane's resonance. By monitoring the resonance one can obtain an indication of the presence of the molecules of interest and in some circumstances an indication of the approximate concentration of these molecules. In addition, several types of moieties having affinities for several different molecules of interest can be placed on the membrane in such a way that the sensor can detect the presence of several different types of molecules of interest and distinguish which ones may be present and which ones may be absent.

30 Claims, 11 Drawing Sheets

OTHER PUBLICATIONS

Stuart W. Wenzel, et al., Flexural Plate-wave Gravimetric Chemical Sensor, Mar. 1, 1990, pp. 700-703, vol. A22, No. 1/3, Elsevier.

Stuart W.Wenzel, et al., A Multisensor Employing an Ultrasonic-Lamb-Wave Oscillator, Jun. 1988, pp. 735-743, vol. 35, No. 6, IEEE Transactions on Electron Devices.

Peter Hsieh, et al., DC Magnetron Reactive Sputtering of Low Stress AlN Piezoelectric Thin Films for Mems Application, 1999, pp. 165-170, Mater. Res. Soc.

Vittorio Ferrari, et al., Multisensor array of mass microbalances for chemical detection based on resonant piezo-layers of screen-printed PZT, Aug. 2000, Elsevier, Switzerland.

E. Defay, et al., PZT thin films integration for the realisation of a high sensitivity pressure microsensor based on a vibrating membrane, Apr. 2002, pp. 64-67, Elsevier.

P.W. Walton, et al., Gravimetric biosensors based on acoustic waves in thin polymer films; 1993, pp. 401-407, vol. 8, No. 9-10, Biosensors & Bioelectronics, U.K.

Allison J. Clark, Lorne A. Whitehead, Charles A. Haynes and Andrzej Kotlicki, Novel Resonant-Frequency Sensor to Detect the Kinetics of Protein Adsorption,Review of Scientific Instruments, Dec. 2002, pp. 4339-4346, vol. 73, No. 12.

W. O. Wong, The Effects of Distributed Mass Loading on Plate Vibration Behavior, Journal of Sound and Vibration, 2002, pp. 577-583.

* cited by examiner

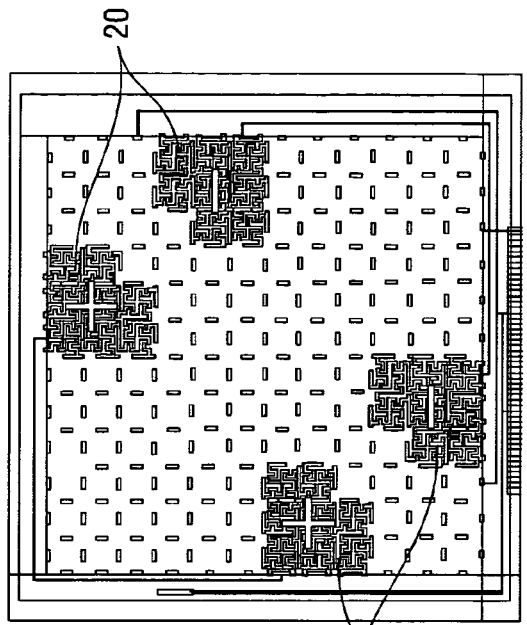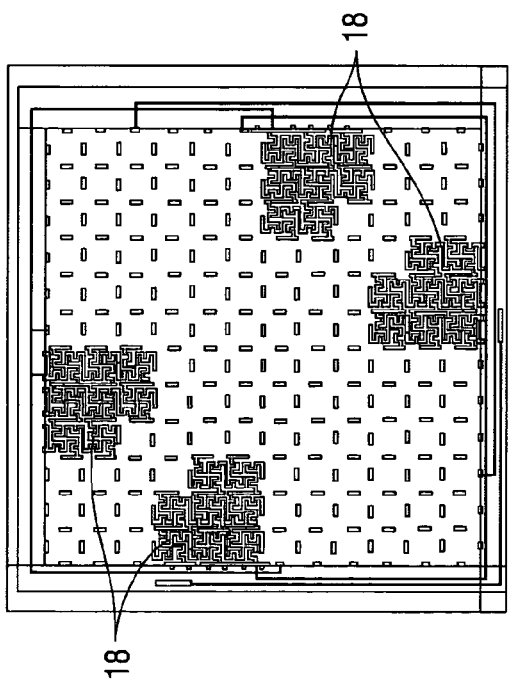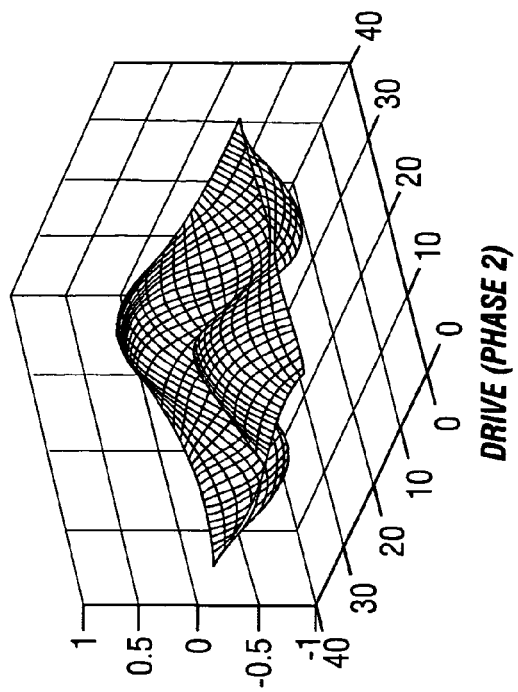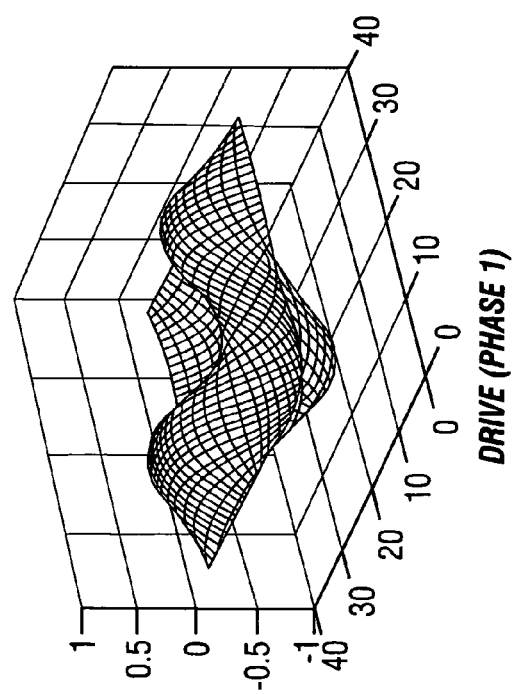
Fig.2A
Fig.2B

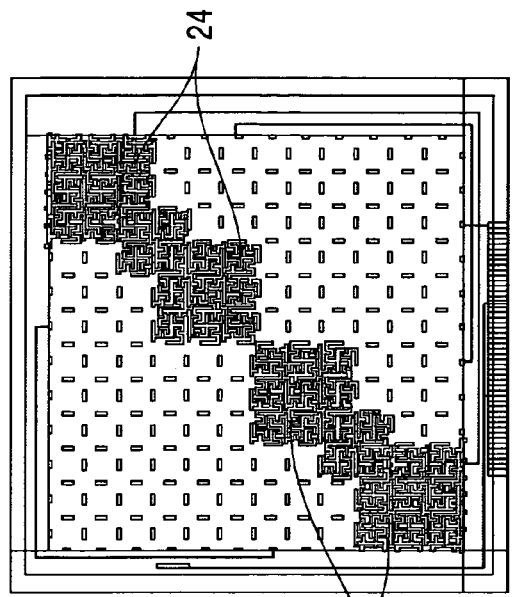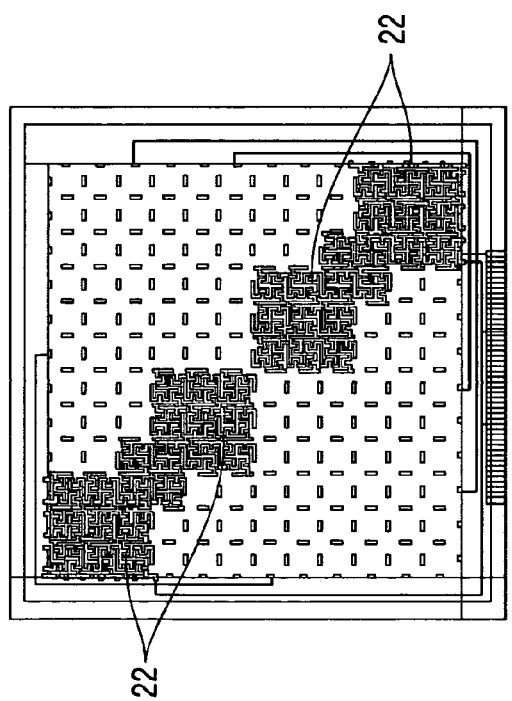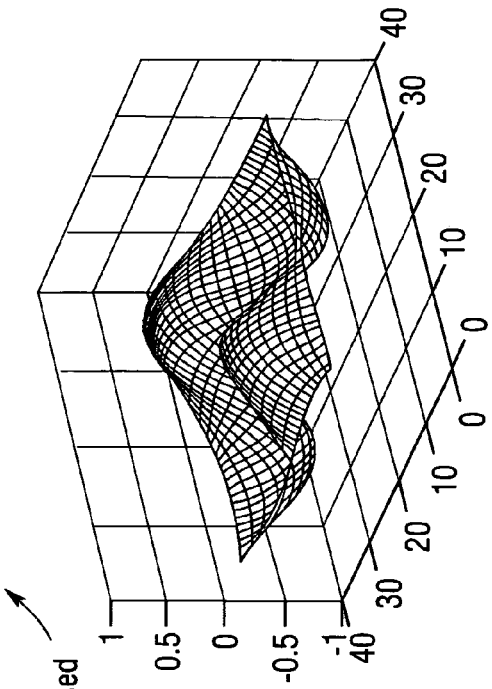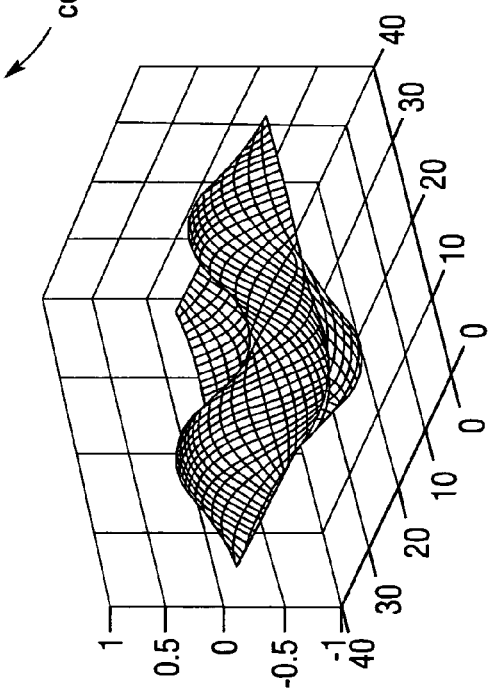
Fig.3B
Fig.3A
Pairs of corners sensed differently

MEMS MEMBRANE BASED SENSOR

CROSS-REFERENCE TO RELATED APPLICATIONS

This application claims priority from U.S. Patent application Ser. No. 60/424,135 filed Nov. 6, 2002 and entitled A MEMS Based Biosensor, the entirety of which is hereby incorporated by reference

STATEMENT REGARDING FEDERALLY SPONSORED RESEARCH

This invention was made with government support under Grant R21 EB000735-01 NAG3-1741 awarded by NIH. The government may have certain rights in this invention.

BACKGROUND OF THE INVENTION

The present invention is directed to sensors and, more particularly, sensors of the type that are fabricated using solid state fabrication techniques such as, for example, complimentary metal oxide semiconductor (CMOS) techniques.

Over the last 30 years, significant improvements have been made in techniques and equipment used to fabricate miniature devices and, consequently, the use of micromachined equipment is widespread in any modern society. Improvements in silicon manufacturing and high-precision machinery opened the area now known as Micro-Electro-Mechanical Systems (MEMS) for research and development of applications. Subsequent development of microscale valves, pumps, channels and heat exchangers allowed for manipulation of extremely small fluid volumes. Coupled with mass fabrication techniques refined in the integrated circuit (IC) and MEMS communities, microfluidic and microchemical systems are now starting to find their way into industrial use.

A major application area is the development of sensors, most of which are custom made. Environmental sensors which continuously monitor their surroundings to provide background statistics and warnings against unhealthy conditions are known to be used in cities, sea and air. In such applications, microscale solutions are sought for reasons of minimum cost and impact as well as long lifetime due to limited use of consumables. More advanced configurations include coordinated and flexible sensor systems with multiple devices operating on a single fluid sample to carry out fully automated chemical analysis with the aid of on-board processing logic. Examples range from DNA separation and analysis arrays to personal chemical warfare sensors. A recent report from the World Technology Evaluation center provides an excellent overview of the different technological approaches used. Common to all sensor projects is the desire to create transducers capable of identifying small amounts of interesting or harmful materials present in their environment. Auxiliary goals include detection speed, robustness, reliability and long life. Widespread use, in particular for routine medical purposes in private homes or developing countries, also requires an inexpensive device that may be operated by unskilled individuals.

The principles of acoustic wave, sometimes referred to as gravimetric sensors, are well known and applications have appeared in the literature for more than a decade. Molecular interactions can be detected electronically through the polarizability of biological macromolecules, optically through the use of fluorescencing tags, radiometrically through the use of radioactive labeled tags, or acoustically. Recently, MEMS based sensors have been incorporated in the biotechnical and biomedical fields. Application of acoustic biosensors range from cell detection, glucose biosensing, antibody-antigen recognition, and protein adsorption.

There are numerous examples of gravimetric biosensors. The basis of detection is the decrease in the resonant frequency of a resonator that occurs as analyte species attach to the resonating element. Analyte specificity is conferred for biological analytes by functionalizing (treating) the exposed surface of the resonator with ligands that recognize and bind to the target analyte species. Examples of suitable binding entities for target biological analytes include antibodies, receptors, lectins, aptamers and oligonucleotides.

Piezoelectric quartz crystal microbalances (QCMs) have been used since the late 1950s to detect gas and liquid phase analytes. Application of QCM technology to biological analytes is more recent. QCMs have been used to track the non-specific adsorption of proteins to unmodified and modified quartz crystal surface electrodes. Immobilization of antibodies to the crystal surface confers analyte specificity.

A wide variety of cantilever, membrane and piezoelectric resonator-based sensors have been fabricated using MEMS technology. Cantilever systems have been used to detect metal deposition and chemical species adsorbing to polymeric coatings (Oden, 1998; Lange et al.1998). Basic modeling approaches for cantilever beam resonances have also been described (Glumac et al., 1995). Reported membrane-based gravimetric chemical sensors typically rely on analyte adsorption to polymer films and polymer coated plates (Walton et al., 1993; Wenzel and White, 1990); recently (Wang et al., 1998) described an antibody-functionalized flexural plate-wave sensor for specific detection of cancer antigens. Finally several different piezoelectric films, operating in a similar manner to the macroscopic QCM devices, have also been proposed as gravimetric chemical sensors (Ferrari et al., 2000; Hsieh et al., 1999)

Sensors for detecting the presence of molecules of interest have application in numerous fields, including medical diagnosis, biomedical research, and detection of agents used in biological and chemical warfare. The need exists for an inexpensive, compact sensor with high sensitivity for these and other applications.

BRIEF SUMMARY OF THE INVENTION

The present invention is directed to a sensor, sensor array, system and method built around the use of a MEMS membrane which has been treated (functionalized) so as to be receptive to a target. Because the MEMS membrane has very low mass, small changes in the mass of the membrane after it has been exposed to a substance which may contain the target can be detected, with the change in mass being attributable to the target being captured by the treated membrane. Such a sensor, sensor array, system and method have a variety of uses. For example, the invention can be used as a biosensor for the specific detection of species such as proteins, carbohydrates, lipids, nucleic acids, toxins, cells, spores, or viruses in fluid phases. Changes in the frequency and/or amplitude response of a vibrating MEMS membrane that has been functionalized by the adsorption or covalent attachment of a binding entity with a specific target such as a receptor, ligand, antibody, lectin, aptamer, nucleic acid, peptide nucleic acid, or imprinted polymer can be detected.

The frequency and/or amplitude response may be determined by driving the membrane with a burst of energy spanning a wide range of frequencies and then tracking the vibration decay or by actively driving the membrane vibrations, sweeping the drive frequency and determining the corresponding vibration amplitudes.

The invention may be used as a gravimetric biosensor wherein the immobilized binding group is located in one or more areas on the surface of the membrane whose locations on the membrane, sizes and areal immobilization densities are designed to maximize the observed frequency and/or amplitude shifts on target analyte binding and to maximize the discrimination between all combinations of specific and non-specific binding. This discrimination may take three forms: (a) change in resonant frequency of the membrane, (b) appearance or disappearance of higher order harmonic vibrations, or (c) change in amplitude decay rates. In such a biosensor, a single membrane may be comprised of a plurality of individually addressable elements for actuation and for sensing purposes. That permits the specific excitement of selected higher order vibrational modes and enables simultaneous vibration actuation and membrane response sensing.

In another embodiment, resistive heaters are provided globally or in individually addressable circuits within the membrane to permit different areas of the membrane to be selectively heated. That may be used with heat-activated chemistries for binding group immobilization and to selectively disrupt binding group—target analyte interactions during sensing. This disruption would be particularly useful in nucleic acid detection scenarios where the binding group is an oligonucleotide or peptide nucleic acid (PNA) and the analyte is a complementary nucleic acid; local heating may be used to melt or disrupt hybrids. The melting temperature is diagnostic of the degree of the complementarity of the immobilized oligo or PNA with the bound nucleic acid. This also offers the possibility of sensor reuse in nucleic acid sensing applications; after a given sample is analyzed, all hybridized nucleic acids may be removed by heating above 94° C.

In another embodiment, a membrane of a MEMS membrane gravimetric biosensor has more than one binding group for different targets immobilized in separate areas on the same membrane. This polyfunctionalization enables the detection of one or more target analytes from complex samples with a single membrane. In another embodiment, the separate areas may have differing areal densities to enable quantization of target analyte species by using a priori knowledge of binding constants in conjunction with the mass of bound analyte as a function of binding group density.

Individual sensors may be combined to form arrays, and arrays may be combined to form systems to enable large-scale discrimination in circumstances where there are multiple possible target analytes. The sensors, arrays, and systems may be provided with a means for delivering a sample to be analyzed.

A method is also disclosed. The method comprises exposing a sensor of the type having a substrate carrying a MEMS membrane to a substance to be analyzed, the membrane having been treated so as to be receptive to a target; actuating the membrane; detecting motion of the membrane; and analyzing the detected motion to determine if the target was found in the substance to be analyzed.

BRIEF DESCRIPTION OF THE DRAWINGS

For the present invention to be easily understood and readily practiced, the present invention will now be described, for purposes of illustration and not limitation, in conjunction with the following figures, wherein:

FIGS. 2A and 2B illustrate actuation of the membrane with certain of the addressable sections shown in FIG. 1;

FIGS. 3A and 3B illustrate sensing of membrane motion with certain of the addressable sections shown in FIG. 1;

DETAILED DESCRIPTION OF THE INVENTION

We have developed a prototype of a sensor consisting of a MEMS membrane treated so as to be receptive to a target. The treatment of the membrane is referred to herein as functionalizing. In our prototype, the MEMS membrane is functionalized with a recognition group (e.g. ligand, receptor, lectin, antibody, aptamer, oligonucleotide, peptide nucleic acid, etc.). Binding of target analyte to the functionalized membrane increases the mass of the vibrating element, resulting in a measurable decrease in its resonant frequency. The functionalized membrane may be used, for example, as a biosensor in a gravimetric detector to directly determine adsorbed mass without probe moieties such as radiolabels or fluorescent tags. Further, this mode of detection permits chip-based sensors to be self-contained as only sample and power need be supplied and provision for signal readout made. Such chip-based sensors will be able to operate with both gas-phase and liquid-phase samples.

The MEMS membrane sensor should have superior sensitivity to that of existing acoustic-wave gravimetric sensors including macroscopic quartz crystal microbalances (QCM) and MEMS-based resonant structures including plates, cantilevers and films. This sensitivity arises from a dramatically increased surface area-to-mass ratio, wherein greater amounts of analyte may be bound to the surface per unit mass of the resonant element, increasing the relative frequency depression for a given amount of adsorbed mass.

The design for the MEMS membrane sensor (see FIGS. 1 and 2) is based on a complementary metal-oxide semiconductor (CMOS) MEMS membrane originally developed at Carnegie Mellon University as a speaker for hearing aid applications. The term MEMS membrane refers to a MEMS mesh that has been sealed. The CMOS MEMS fabrication steps for the non-functionalized MEMS membrane are described in U.S. Pat. No. 5,717,631 (issued on Feb. 10, 1998 and incorporated herein in its entirety by reference) and in U.S. patent application Ser. No. 08/943,663 (filed on Oct. 3, 1997 and issued on May 20, 1999 also incorporated herein in its entirety by reference). A hearing aid application of this technology titled "Direct Digital Earphone", is described in U.S. patent application Ser. No. 10/222,242, filed on Aug. 16, 2002 and is also incorporated herein in its entirety by reference. Another United States patent application titled "MEMS Digital to Acoustic Earphone with Error Cancellation, filed Sep. 13, 1999, and having a Ser. No. 09/395,073, as well as its foreign counterpart PCT patent application serial number PCT/US 00/25062, filed Sep. 13, 2000, are also incorporated herein in its entirety by reference.

Figure 1A:
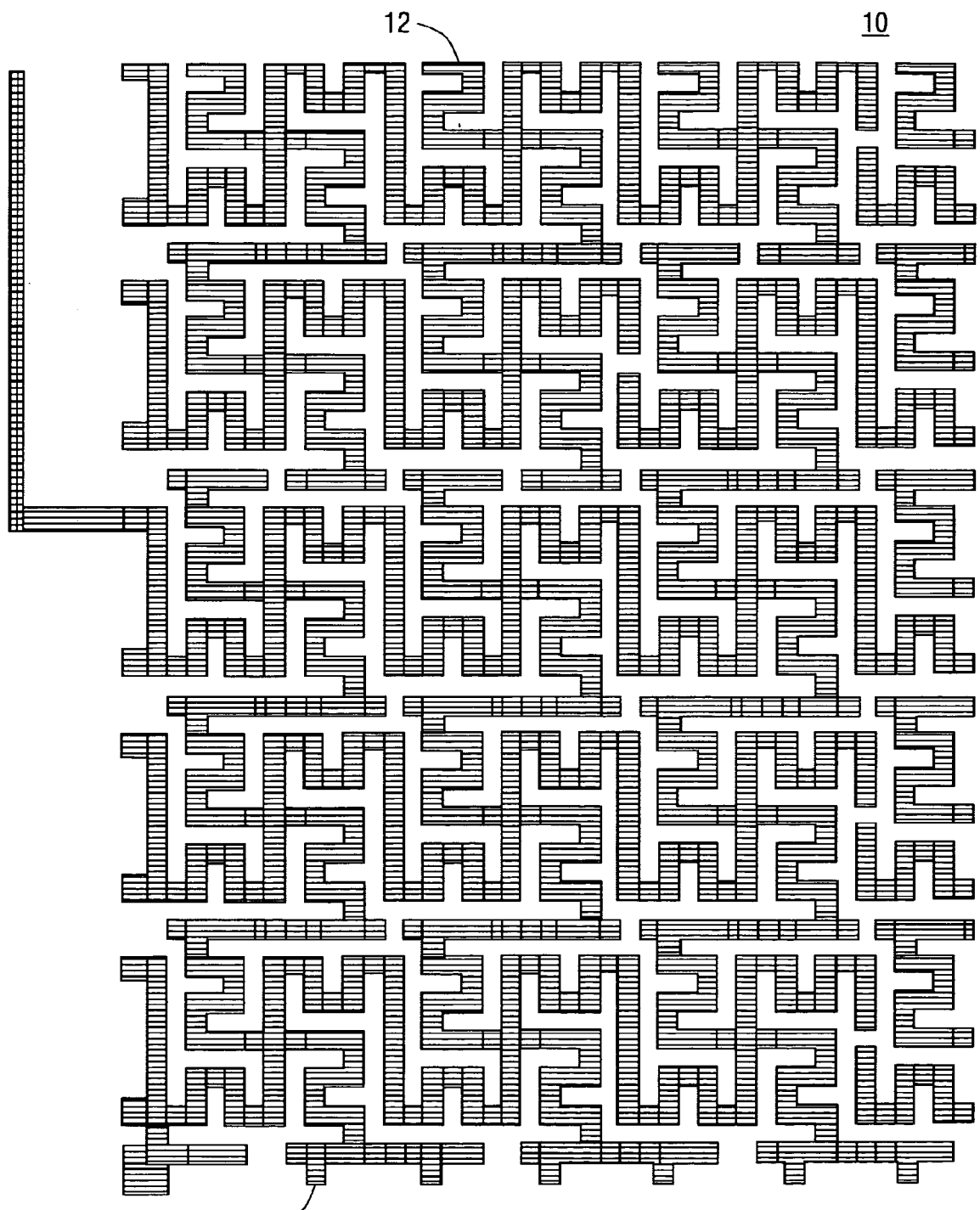
FIGS. 1A and 1B illustrate a mesh which is subdivided so as to provide sections that are individually addressable by metal contacts and vias formed in a different metal layer.
Figure 1B:
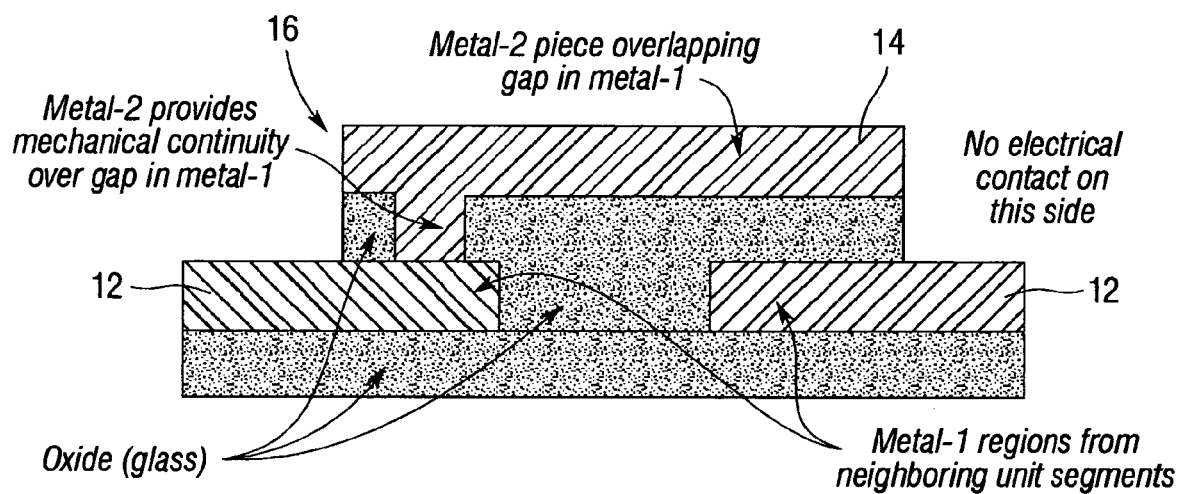

For the sensor of the present invention, the prior art MEMS membrane is modified so that portions of the membrane may be driven (actuated) and the membrane vibrations may be sensed or detected with other portions of the membrane. That is accomplished by modifying the metal mesh that both supports the completed polymer membrane and acts as an embedded electrode. In the prior MEMS speaker applications, the metal mesh acts as a single electrode; in the invention disclosed herein this metal mesh 10 is subdivided into a group of smaller, electrically distinct segments or electrodes 12, as shown in FIG. 1A. That modification enables segments 12 of the mesh 10 to be individually addressed electronically. As shown in FIG. 1B, contacts 14 running in a separate layer of metal 16 may be provided for mechanical support and/or by connection to one end of an electrode 12, ensure that the electrode 12 does not carry unknown electrical charge.

By having separately addressable electrodes 12, selected portions of the membrane can be actuated (see FIGS. 2A and 2B) and other portions of the membrane can be used to detect vibrations (see FIGS. 3A and 3B). In FIG. 2A, four segments 18 act as a driver for actuating the membrane for one phase while in FIG. 2B four different segments 20 act as a driver for actuating the membrane for a second phase. In FIG. 3A, four segments 22 act as a detector for detecting motion of the membrane in response to one phase while in FIG. 3B four different segments 24 act as a detector for detecting motion of the membrane in response to a second phase. In FIGS. 2A, 2B, 3A and 3B we both actuate and detect in a quadrapole mode using four electrodes for actuating and four electrodes for detecting, while using different electrodes for different phases. Neighboring electrodes may be actuated with equal and opposite voltage to reduce feedthrough to the sensing circuit. Alternative configurations where the membrane is actuated either by providing an adjacent driven, resonant element or by placing the entire sensor on a resonator are possible. A checkerboard arrangement of electrodes that actuate vibration electrostatically and electrodes that detect membrane motion capacitively can be provided.

The analyte detection limits of a sensor will depend on both the biophysical properties of the ligand-ligate-membrane system, in terms of the mass of target analyte bound, as well as the inherent sensitivity of the device. The mass of ligand binding to the functionalized MEMS membrane ($M_L$ in g ligand per $cm^2$) will be a function of the molecular weight of the ligand ($M_w$ in g/mol), the total surface number concentration of immobilized binding ligates or receptors ($B_0$ in mol ligate per $cm^2$), the dissociation equilibrium constant of the ligate-ligand pair ($K_d$ in molar concentration), the total surface number concentration of non-specific binding sites ($S_0$ in mole sites/$cm^2$), the dissociation equilibrium constant for non-specific binding ($K_{ns}$ in molar concentration), and the concentration of ligand in solution (L in molar concentration). Assuming the interaction of ligand and ligate is one-to-one, a mass balance on ligand, ligate and binding sites gives $$M_L = M_w \left[ \left( \frac{B_0 L}{K_d + L} \right) + \left( \frac{S_0 L}{K_{ns} + L} \right) \right].$$

We can manipulate the membrane surface and solution conditions such that either the dissociation constant for non-specific interactions is very large ($K_{ns} \gg L$) or such that the number of non-specific binding sites is very small relative to the number of immobilized ligate molecules ($S_0 \ll B_0$) so that we can ignore non-specific interactions. Functionalization of surfaces with a methoxyl-terminated poly-ethylene glycol monolayer has been shown to substantially reduce non-specific protein adsorption when using gold-thiol binding chemistry (Wilcox, 2002).

The inherent sensitivity of the MEMS membrane sensor compares favorably to QCM and cantilever-based sensors. The resonant frequency for a mass with uniform mass loading may be represented as a simple harmonic oscillator and shown to be inversely proportional to the square root of its mass (M). By performing a leading order Taylor series expansion, one may show that the change in resonance frequency ($\Delta f$) relates to the change in mass ($\Delta M$) as $$\Delta f \propto \frac{\Delta M}{M^{3/2}} \propto \frac{SA}{M^{3/2}}$$

where the second proportionality assumes that the amount of immobilized ligand is proportional to the surface area (SA) and is reasonable for a uniform monolayer of ligate. A QCM has a surface area to areal density ratio of about 0.94 $g^{-1}$. For a QCM operating at a nominal frequency of 5 MHz has sensitivity of 17.7 ng/($cm^2$ Hz), and a typical frequency noise level in solution of about 0.2 Hz, this translates to a lower detection limit of about 3.5 ng/$cm^2$. The MEMS membrane disclosed herein has an areal density, for example, of 0.2 mg/$cm^2$ and an active area of, for example, $(130 \, \mu m)^2$ yielding a surface area to areal density ratio of 8.4 $g^{-1}$ or nearly ten times that of the QCM. The membrane also resonates at a frequency around 30–300 KHz, depending on the membrane size and thickness, thus the relative frequency change $$\left( \frac{\Delta f}{f} \right)$$

from changes in mass-loading due to surface adsorption is a least two orders of magnitude higher than a QCM.

Figure 4:
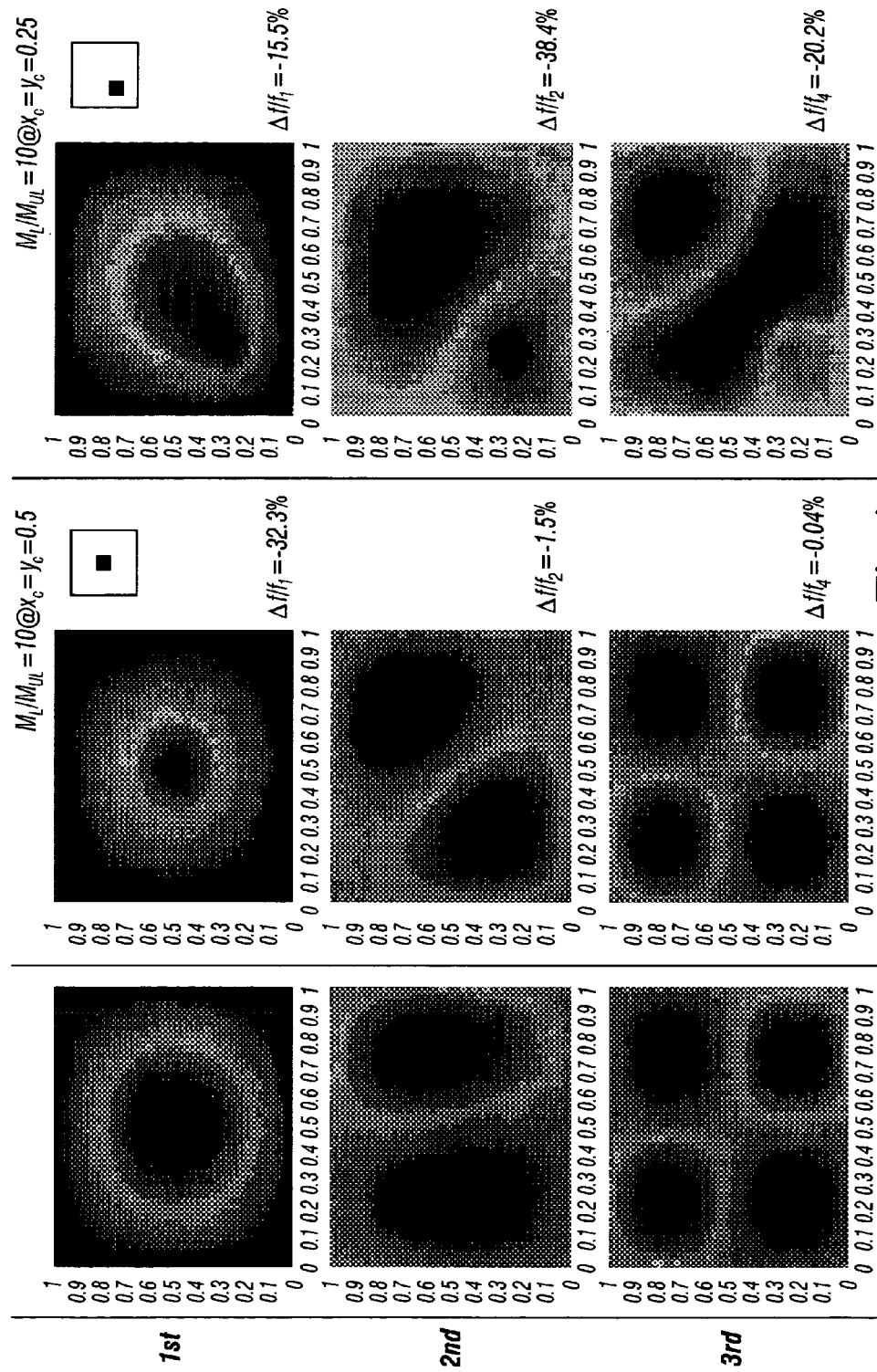
FIG. 4 illustrates relative shifts in resonance frequencies for uneven mass distributions.

To maximize the difference between the mass of an unloaded and loaded device, one would normally provide binding sites of the same type and density across the full surface area available. However, due to the extreme sensitivity of the MEMS membrane to the location of an attached mass, this is not necessarily the best design approach. FIG. 4 demonstrates the effect of a localized change in mass loading for selected eigen-frequencies with relative frequency changes of up to forty percent; at least four orders of magnitude higher than the estimated detection limit. The ratio of loaded ($M_l$) to unloaded ($M_{UL}$) membrane surface shown is ten; this corresponds to a large target molecule binding to a small receptor on the surface. However, similar results are obtained with a substantially smaller $$\frac{M_l}{M_{UL}}$$

ratio and may be enhanced by expanding the area of the functionalized "surface patch" or increasing the functionalization density. The effect of functionalization geometry not only allows for detection when the total amount of target species is small, but also creates the possibility of intrinsically multiplexing devices where a single membrane may have two or more functionalized "areas" on the surface and be able to simultaneously discriminate between the presence of two or more target molecules in solution.

We have built on-chip membranes by using the CMOS-MEMS process described above to create a metal and oxide mesh which is suspended above the substrate by a distance of about 10–20 microns. A serpentine-spring pattern (see FIG. 1A) was designed to circumvent the residual stress problem inherent in large CMOS-MEMS structures. Buckling is thus kept to a minimum: for the original 1.4 mm mesh (roughly equal thicknesses of aluminum and glass) buckling was measured between 10 and 20 microns out of plane, and for a 320 micron mesh, consisting mainly of a single metal layer, it was measured to be about 2 to 3 microns out of plane. This mesh acts as a "skeleton" defining the shape of the membrane. The beams, and gaps between beams, are about 0.9 microns wide. Using chemical vapor deposition (CVD), 0.5 to 1.5 microns thick film of polymer are deposited on the surface of the mesh, creating an airtight seal. The resulting membrane has an areal density of about $2 \times 10^5$ ng/cm$^2$.

The high performance of CMOS circuitry is well established for devices such as accelerometers. This high performance is due to the ability to place sensing circuitry very close (30–50 microns) to the sensing structure, minimizing stray capacitance and maximizing sensitivity. Also, high frequency modulation/demodulation schemes can nearly eliminate low-frequency noise (such as 1/f noise) at the sensor level. Capacitive sensing schemes are by far the most popular, though piezoresistive methods are also possible. We expect to use capacitive sensing schemes whenever possible.

The goal of the on-chip circuitry in our gravimetric sensor is to measure the oscillatory motion of the membrane after it is excited with a force impulse. One needs to measure the frequency of oscillation and the amount of damping, both of which give information about the composition and mass of the species that is adsorbed on the membrane. It is possible to use on-chip digital signal processing (DSP) to examine the signal and make the chemical analysis, and provide a simplified output to the user. The low cost of mass produced CMOS sensors with this kind of built-in data reduction would make massive parallel gathering of experimental data both economical and simple to implement.

Figure 5:
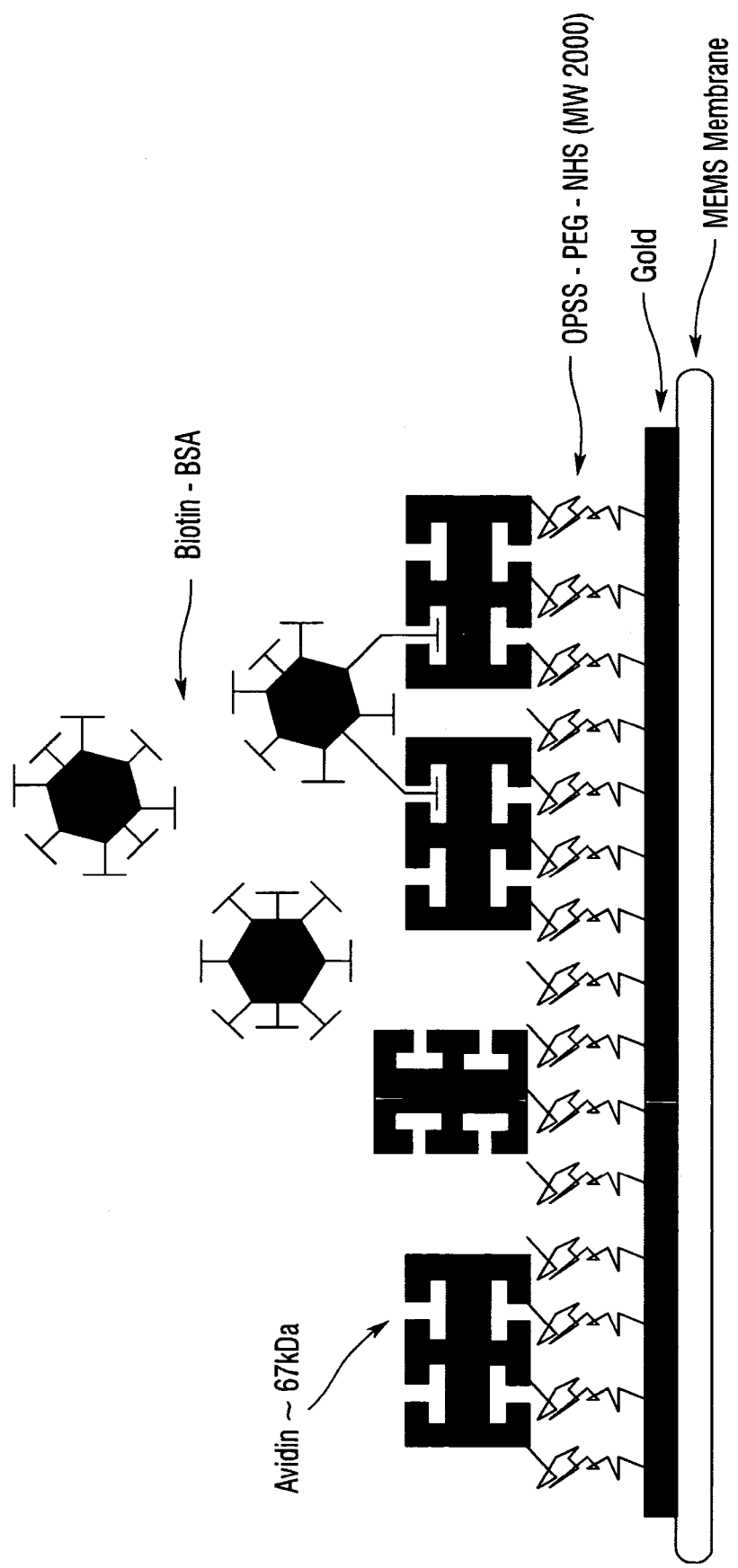
FIG. 5 illustrates one type of functionalization chemistry based on the use of a layer of gold.

One possible approach to the functionalization of the MEMS membrane is to coat the surface of the membrane with a thin layer of gold, followed by chemisorbed monolayer of an activated thiol to which protein may be covalently attached. A specific example of this type of approach is shown in schematic form in FIG. 5. In this example an co-functionalized thiol monolayer, orthopyridyl-disulfide-poly (ethylene glycol)-N-hydroxysuccinimide ester (OPSS-PEG-NHS), is chemisorbed onto a thin gold layer that has been deposited on the MEMS membrane. The NHS moiety of the thiol may then be reacted with primary amino groups on the surface of a binding group, in this case the protein avidin, to covalently link the binding group to the surface. Avidin binds biotin specifically and strongly; dissociation equilibrium constants for the avidin-biotin binding interaction are on the order of $10^{-15}$ molar. The functionalized surface is now prepared for the specific binding of target species containing biotin; FIG. 5 shows a multi-biotinylated bovine serum albumin as a model target species.

Figure 6:
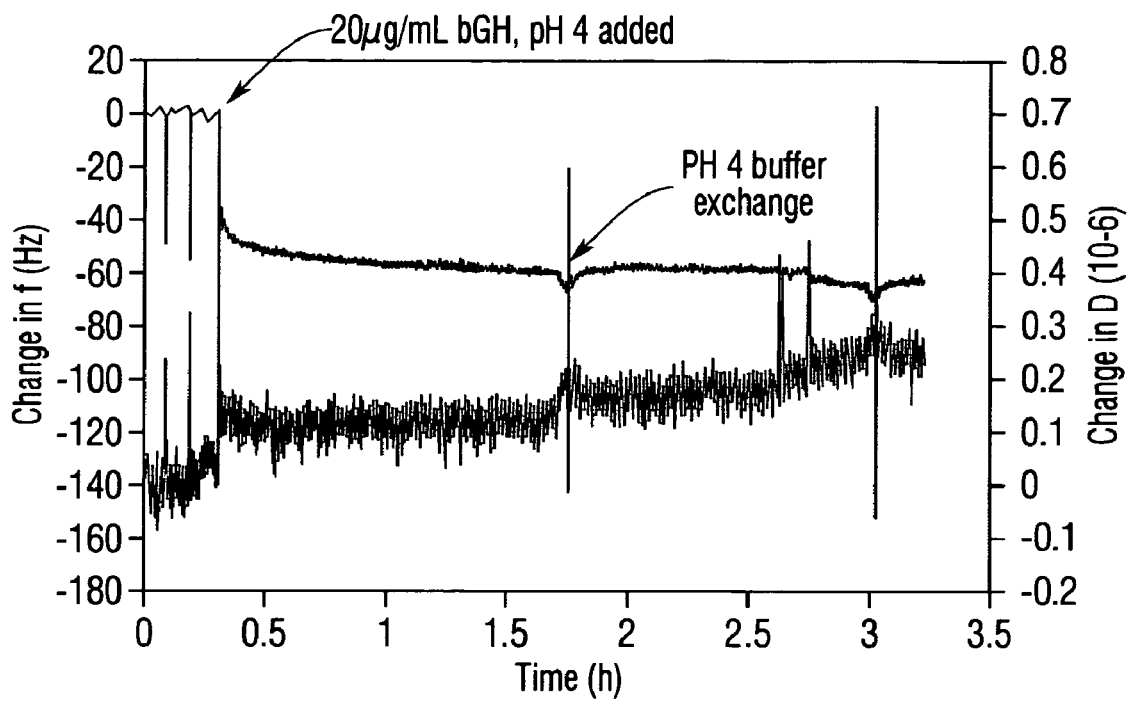
FIG. 6 illustrates nonspecific bovine growth hormone (bGH) adsorption to a hydroxl terminated alkanethiol monolayer, mercaptoundecanol followed using QCM-D. Both the resonant frequency depression and dissipation factor are shown. Roughly 55 ng/cm$^2$ of bGH adsorbed.
Figure 7:
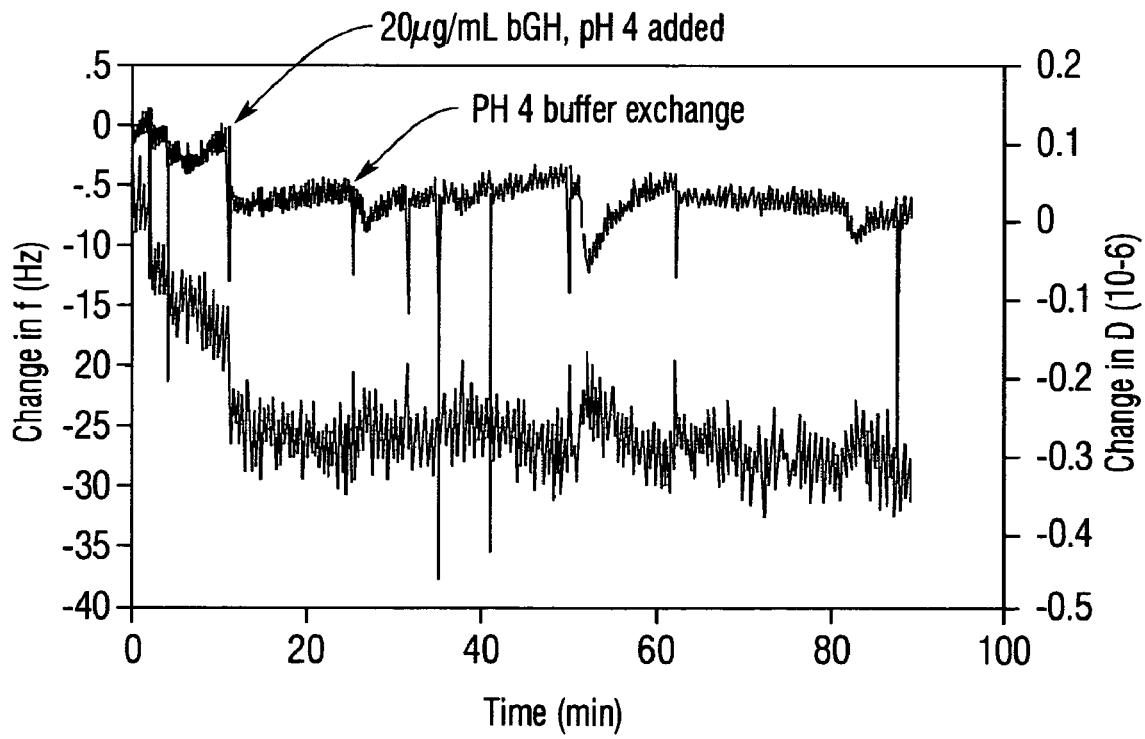
FIG. 7 illustrates nonspecific bGH adsorption to methoxy-PEG$_{5000}$-thiol monolayer followed using QCM-D. Both resonant frequency depression ad dissipation factor are shown. Roughly 8 ng/cm$^2$ of bGH adsorbed.

We have metalized the CMOS MEMS membrane chip by evaporation of gold without damaging the membrane. We have validated this chemistry using a commercial quartz crystal microbalance, the QCM-D by Q-Sense, AB (Västra Frölunda, Sweden). The selection of OPSS-PEG-NHS as an appropriate activated thiol was motivated by the tendency of poly(ethylene glycol) modification of surfaces to reduce nonspecific protein adsorption (Wilcox, 2002). Hydrophilically-terminated SAMs of mercaptoundecanol resulted in significant nonspecific protein adsorption as evidenced by the large resonant frequency depression, roughly –60 Hz or about 55 ng protein/cm$^2$, after exposure of the SAM-coated crystal to a 20 μg/mL solution of bovine growth hormone (bGH) in a Q-Sense QCM-D device with a 5 MHz quartz crystal; the response of the Q-Sense device is shown in FIG. 6. Functionalization of the crystal with a methoxyl-terminated poly(ethylene glycol) [PEG] monolayer gave much better performance; a frequency change of roughly –5 Hz, or about 8 ng protein/cm$^2$, was observed under the same protein exposure conditions as shown in FIG. 7. The PEG layer has much greater resistance to nonspecific protein adsorption as expected from numerous studies in the literature of the passivation conferred by "PEGylation".

Figure 8:
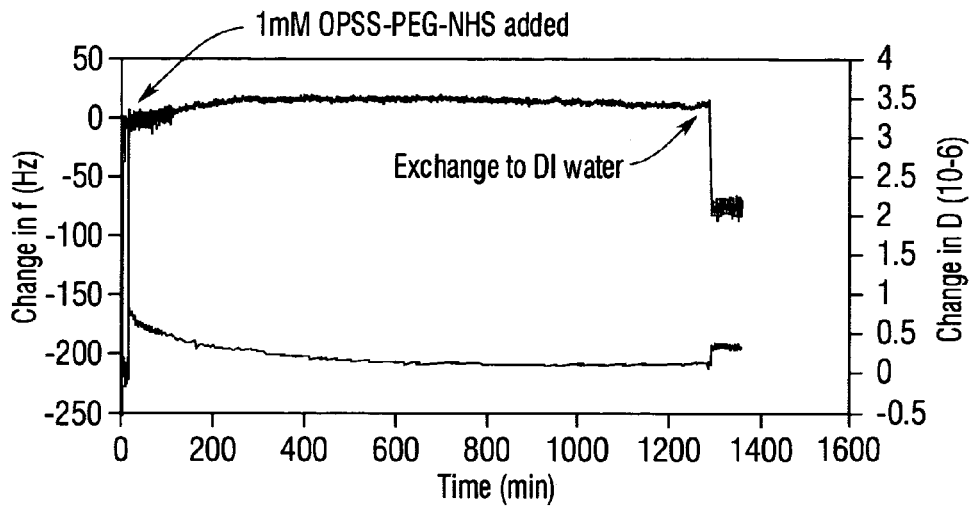
FIG. 8 illustrates the in situ thio-PEG$_{2000}$-NHS monolayer formation followed using QCM-D. Roughly 207 ng/cm2 of PEG$_{2000}$-NHS was immobilized.
Figure 9:
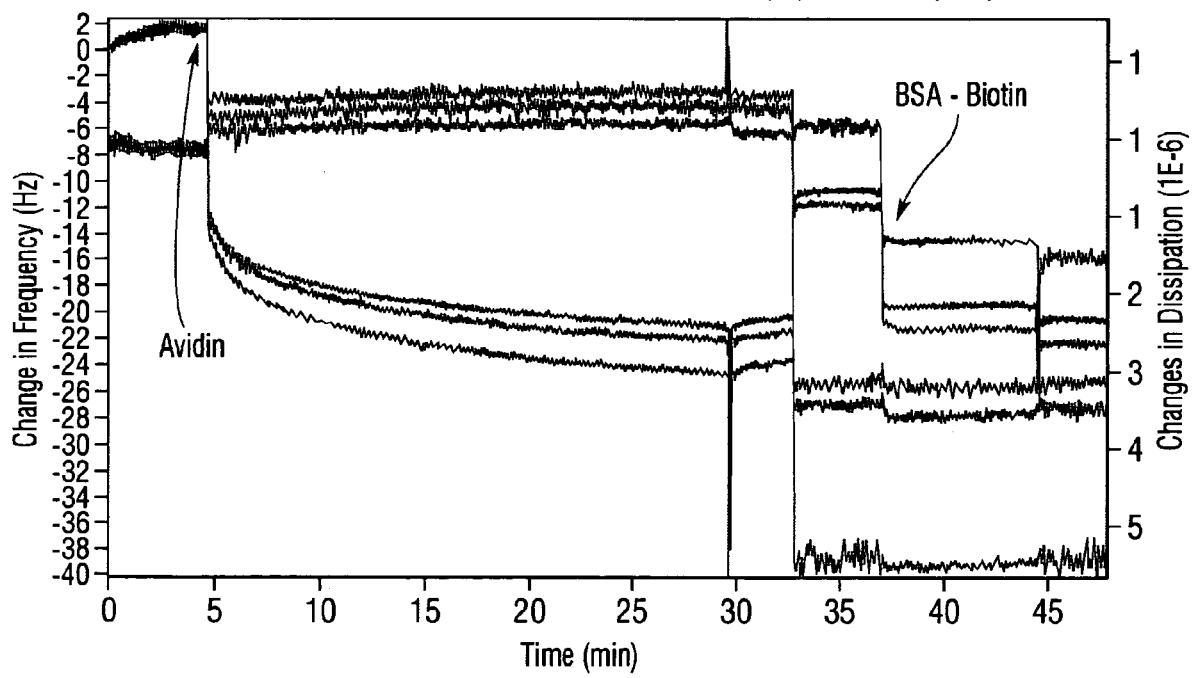
FIG. 9 illustrates the in situ functionalization of the thio-PEG$_{2000}$-NHS monolayer by covalent attachment of avidin and subsequent binding of a target species, biotinylated bovine serum albumin, followed using QCM-D.

We can follow both the formation of the ω-functionalized PEG thiol monolayer, as shown in FIG. 8 and the subsequent immobilization of protein, in this case avidin, as shown in FIG. 9. Roughly 300 ng/cm$^2$ of avidin was covalently attached as shown by the sharp, 20 Hz, decrease in frequency on exposure of the OPSS-PEG-NHS-modified surface to avidin at about 5 min. This immobilized material was stable to a neat buffer wash at about 30 min. At 33 minutes, the buffer solution was changed, resulting in both a frequency and dissipation change. Subsequent exposure of the functionalized crystal to the target species at about 37 minutes resulted in a further decrease in frequency of 10 Hz, corresponding to the binding of about 150 ng/cm$^2$ of the biotinylated bovine serum albumin target species. Both the resonant frequency and dissipation factor are shown. This demonstrates that this protein immobilization route is viable. Based on this and other work, immobilized proteinacious ligand densities on a functionalized membrane are on the order of 250 to 500 ng/cm$^2$ for a binding protein of nominal 20 to 60 kDa molecular weight.

Another possibility for functionalizing the membrane is to chemically modify the membrane polymer itself to enable subsequent covalent attachment of binding moieties. If Parylene is used as the membrane-forming polymer, the Parylene may be modified photochemically. Barie and coworkers (Barie et al., 1998) report the use of aryldiazirine-functionalized bovine serum albumin as a light-activated linking agent. Admixtures of dextran and linking agent were photopolymerized resulting in the deposition of a dextran film to which proteins could be immobilized via primary amino groups using standard carbodiimide chemistry. This dextran-mediated approach may have the added benefit of reducing non-specific binding to the membrane via steric interactions. Weisenberg and Mooradian (2002) have recently assessed the hemocompatibility, an indicator of inertness, of Parylene films and have found them to be comparable to $SiO_2$ and polyurethanes.

Figure 10:
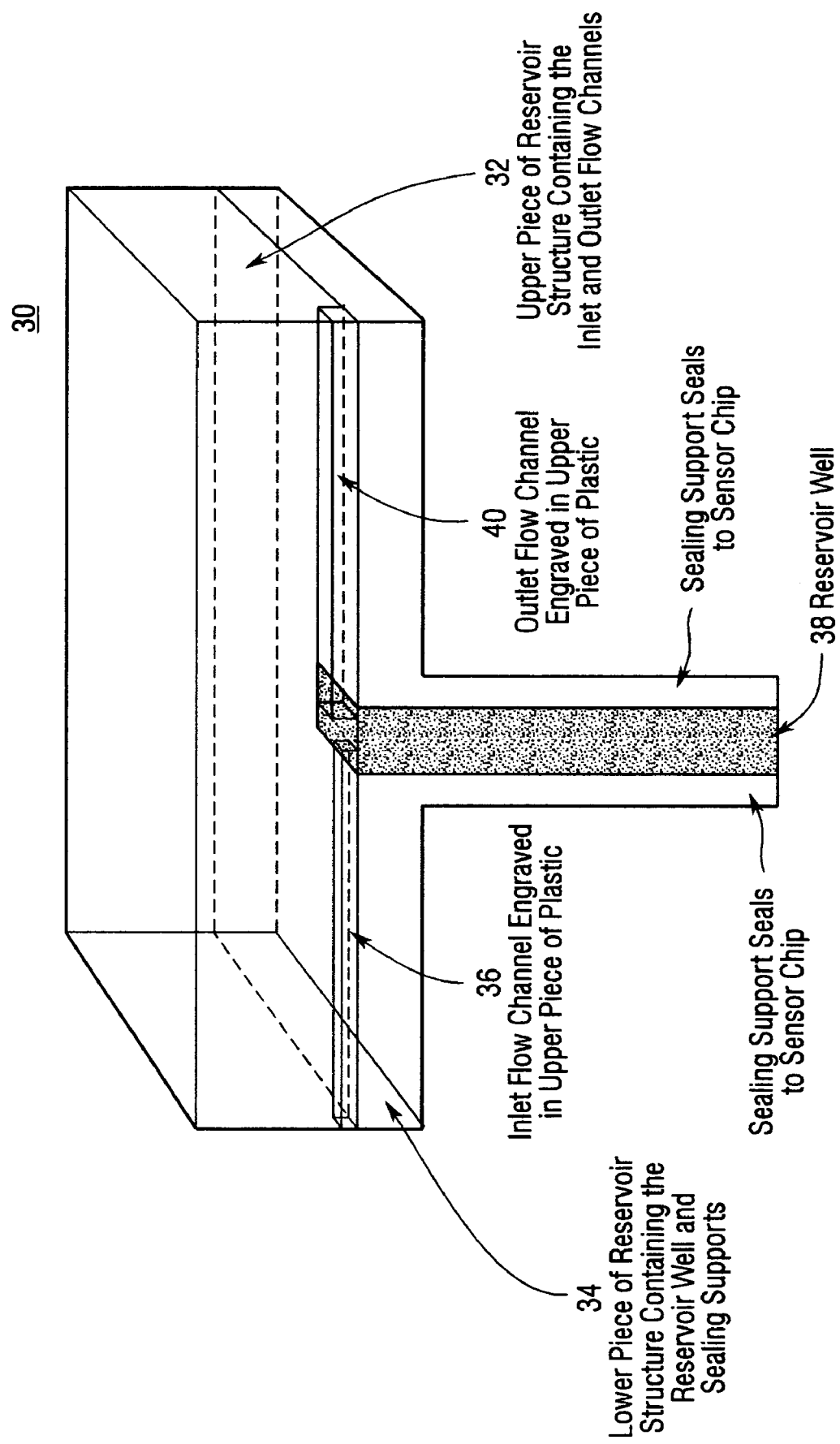
FIG. 10 illustrates a system in which a sensor, sensor array, or array of sensor arrays may be brought into contact with a liquid sample.

The sensor membrane must be brought into contact with a fluid buffer containing the samples to be tested. Any suitable system for enabling such contact may be used. One exemplary system 30 is illustrated in FIG. 10. In FIG. 10, an upper portion 32 and a lower portion 34 are provided. The upper portion 32 and lower portion 34 collectively provide an input port 36 connected to a reservoir 38, which is connected to an output port 40. A sensor chip (not shown) is held in such a manner that the sensor's membrane(s) are in contact with the fluid buffer, but the electronics of the sensor are shielded from the fluid buffer. The sensor chip may be a sensor having a single sensing membrane, an array of membranes, or an array of such arrays. Further, at least certain of the membranes may have more than one area that has been functionalized.

The present invention is also directed to a method comprising: exposing a sensor of the type having a substrate carrying a MEMS membrane to a substance to be analyzed, the membrane having been treated so as to be receptive to a target; actuating the membrane; detecting motion of the membrane; and analyzing the detected motion to determine if the target was found in the substance to be analyzed. In the disclosed method, it is necessary to perform two basic functions, exciting the membrane with an impulse, and measuring its response.

Excitation can be accomplished in several ways. Already demonstrated in the case of the microspeakers is electrostatic actuation. The metal in the membrane's mesh structure can be charged so that the electric field between the membrane and substrate produces an attractive force. This force would be applied long enough to pull the membrane to the substrate, and then released. At this point the membrane would vibrate freely, with damping mainly from the surrounding fluid.

A second method of actuation is thermomechanical. One can use the polysilicon layer in the CMOS process to build resistors within the membrane, and heating the membrane with an electric current will cause deflection of the beams due to differences in thermal expansion between the aluminum and silicon dioxide (glass) materials. This requires more power, but possibly lower voltages than the electrostatic actuation.

A third method of actuation is to build a separate, external, device on which the sensing membrane is mounted. The external device could be either a MEMS device optimized for large impulses, or some other type of device such as quartz crystal or piezoelectric film. The force impulse would be transferred to the membrane via its inertia relative to the moving support structure.

A fourth method of actuation is use an external resonating element. In this scenario, the external element is placed in communication with the fluid reservoir. The fluid sample itself would transmit vibrations from the external element to the membrane, providing the actuation.

There are several possible modes of detecting the vibrational frequency of the membrane. The metal mesh supporting the membrane may be used as an electrode and paired with a second electrode on the other side of the air gap under the membrane; membrane vibrations may be sensed via the variation in capacitance between the two electrodes as the spacing between the electrodes changes with membrane motion. The metal mesh itself may incorporate piezoresistive elements that respond to changes in the membrane tension as the membrane vibrates. In addition, direct optical detection of membrane vibration is possible with interferometric or reflective techniques (C. Q. Davis and D. M. Freeman, "Using a light microscope to measure motions with nanometer accuracy", Optical Engineering, pp 1299–1304, 1998).

The CMOS MEMS device may have one or many membranes. There are several reasons for using multiple membranes, e.g. multiple membranes that are identical may serve to lower the noise floor of the device by averaging signals. This is a useful technique in the MEMS world, as it is often very simple to design many instances of a given structure, and exploit the uniformity in processing and material properties over a small area to obtain high performance. Another reason to use multiple membranes is redundancy so that a faulty membrane may be ignored. Still another reason for multiple membranes is that we may functionalize them for different species, thus making one device that can perform multiple analyses.

Finally, it should be noted that by using the polysilicon resistors we can control the temperature of the membranes, and take data as a function of temperature to obtain another dimension of information about the chemistry of the solution.

Figure 11:
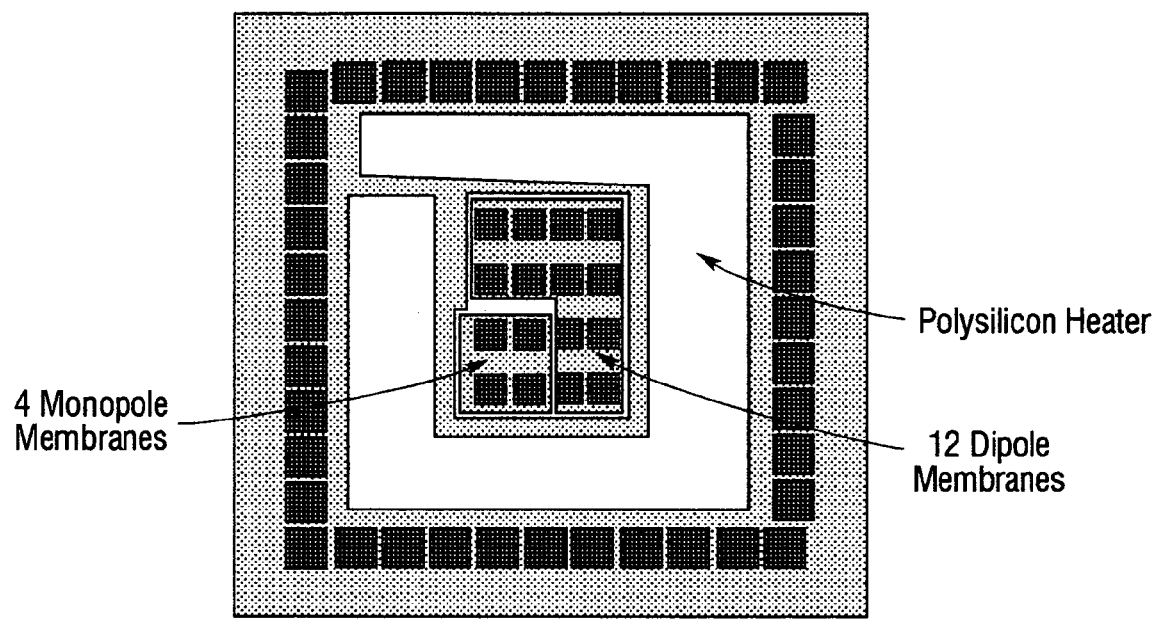
FIG. 11 illustrates a chip having sixteen independent membranes.

FIG. 11 illustrates a completed chip having sixteen independent MEMS membranes, each of which may be functionalized to one or more different targets. In this embodiment, the membranes are 132 μm on a side. A polysilicon heater is provided under empty areas to facilitate testing temperature effects on the chemistry. In this embodiment, twelve of the membranes are dipole membranes while four of the membranes are monopole membranes.

Figure 12:
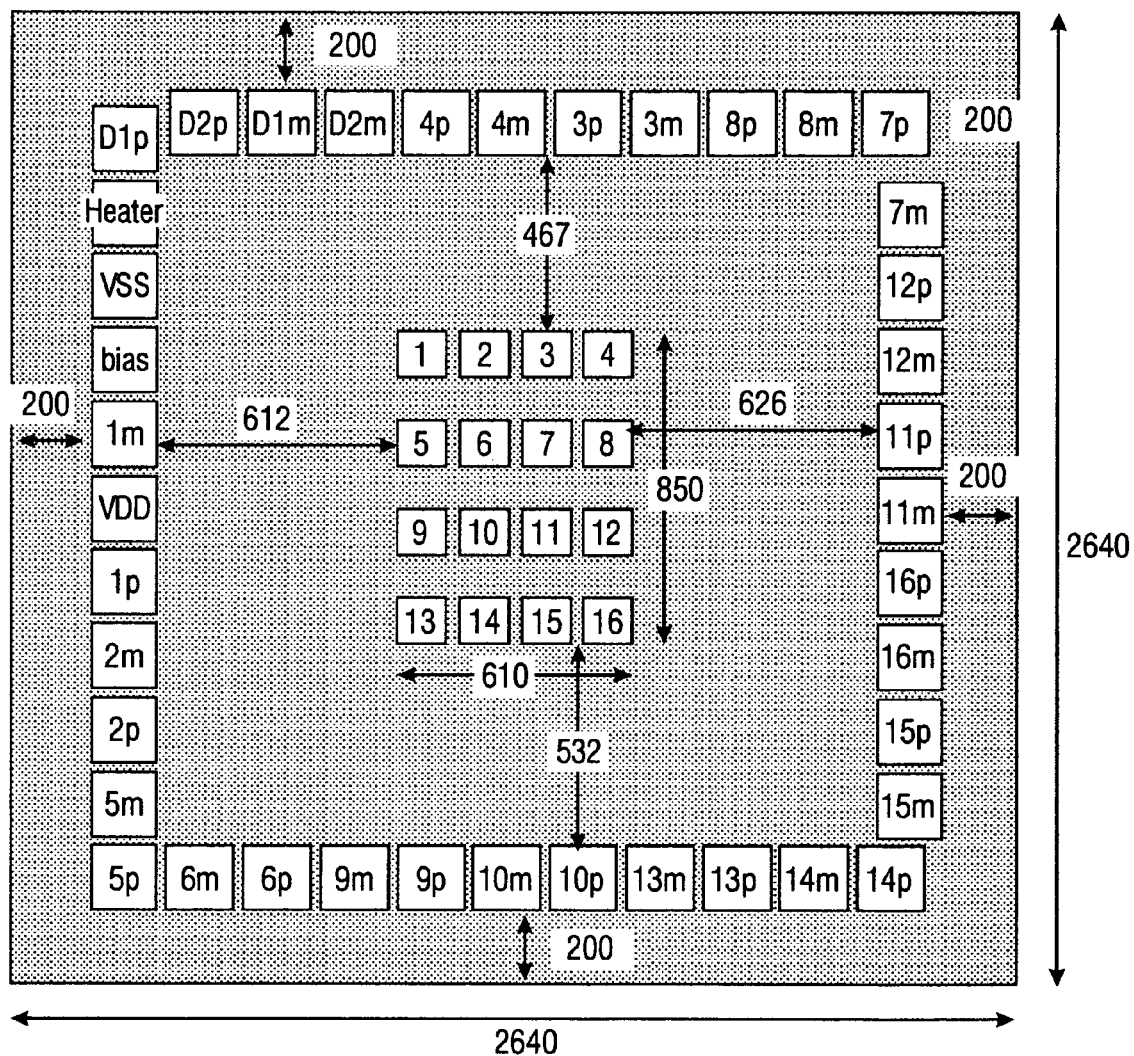
FIG. 12 illustrates the chip dimensions and labels.

FIG. 12 illustrates various chip dimensions and labels. Pins D1x and D2x are the two phases while pins Dxp and Dxm are the two polarities of the drive voltage. The heater connects to a 1200 ohm poly resistor fabricated around the devices. VSS may be set to ground (zero) volts and VDD to the power supply (e.g. 3.3 volts). Power for the chip is approximately 93 mW. Pins 1m and 1p are the differential output of sensor 1. Sensors 9, 10, 13 and 14 are monopole while the remainder of the sensors are dipoles.

Multi-target arrays will be used when the goal is to simultaneously detect the presence of multiple species in a single sample. Given a list of N possible targets, we seek to determine how to discriminate between all of the N! possible combinations present. Auxiliary objectives—in addition to sensitivity—including minimizing the physical size of the arrays as well as the cost and effort required to fabricate and functionalize the detection elements present. Typically, one would expect this to be achieved by selecting a configuration with a minimum number of binding sites while retaining a sufficient binding capacity to generate a positive signal for each target species. It is also of interest to determine the minimum number of harmonics one needs to actuate to achieve a well separated set of frequency shifts.

Associated with the actual device design, one could also imagine using embedded logic controllers to dynamically determine the order in which actuation sequences should be executed. The ability to identify situations where a full frequency sweep is not needed would reduce power consumption and sampling time and thus extend the life-span of continuous monitoring devices.

Redundant arrays will be used when the goal is to get two or more independent measurements from the same fluidic sample. In single-target systems, redundancy is trivially achieved by device replication. However, in a complex multi-target array designed to scan a sequence of eigenfrequencies and use the absence of a particular response to indicate a (mis)match, duplication implies a higher binding capacity and thus lower sensitivity.

Auxiliary objectives in design for redundancy will seek to maximize remaining discrimination capabilities when any part of the sensor array malfunctions or produce spurious results. This is mostly relevant for autonomous monitoring devices or for sensor arrays operating without the supervision of experts capable of realizing that something is wrong.

While the present invention has been described in connection with preferred embodiments thereof, those of ordinary skill in the art will recognize that many modifications and variations are possible. The present invention is intended to be limited only by the following claims and not by the foregoing description which is intended to set forth the presently preferred embodiment.

What is claimed is:

1. A sensor array, comprising:
   a substrate;
   a plurality of sealed micromachined mesh membranes carried by said substrate, a recognition group attached to said membranes, said recognition group being receptive to a target;
   a plurality of drivers for actuating each of said plurality of membranes; and
   a plurality of detectors for detecting motion of said membranes.

2. The sensor array of claim 1 wherein at least certain of said membranes have a plurality of areas, each of said plurality of areas having a recognition group attached to said areas, said recognition group being receptive to a target.

3. The sensor array of claim 2 wherein certain of said plurality of areas having a recognition group attached to said areas responsive to different targets.

4. The sensor array of claim 2 wherein certain of said plurality of areas have one of different areal densities and different sizes.

5. The sensor array of claim 1 wherein certain of said plurality of membranes having a recognition group attached to said membranes responsive to different targets.

6. The sensor array of claim 1 additionally comprising a layer of gold covering at least a portion of certain of said plurality of membranes.

7. The sensor array of claim 1 wherein said drivers include one of a plurality of electrostatic drivers and a plurality of resonating elements in contact with said membranes.

8. The sensor array of claim 1 wherein said detectors include one of a plurality of capacitive, a plurality of piezoresistive, a plurality of piezoelectric, and a plurality of optical detectors.

9. The sensor array of claim 1 additionally comprising analyzing circuitry responsive to said plurality of detectors.

10. The sensor array of claim 1 additionally comprising resistors positioned to heat at least a portion of a least certain of said membranes.

11. A system, comprising:
    a sensor comprising:
    a substrate,
    a sealed micromachined mesh membrane carried by said substrate,
    a recognition group attached to said membrane, said recognition group being receptive to a target;
    a driver for actuating said membrane; and
    a detector for detecting motion of said membrane; and
    a delivery system for delivering a fluid for analysis to said sensor.

12. The system of claim 11 wherein said delivery system includes an input port, a reservoir connected to said input port, and an output port connected to said reservoir, at least a portion of said membrane being exposed to the fluid in said reservoir.

13. The system of claim 11 wherein the walls of said delivery system are not receptive to the target.

14. A system, comprising:
    a sensor comprising:
    a substrate;
    a sealed micromachined mesh membrane carried by said substrate,
    a recognition group attached to said membrane, said recognition group being receptive to a target; and
    a detector for detecting motion of said membrane;
    a delivery system for delivering a fluid for analysis to said sensor; and
    a driver for acting upon a fluid in said delivery system.

15. The system of claim 14 wherein said delivery system includes an input port, a reservoir connected to said input port, and an output port connected to said reservoir, at least a portion of said membrane being exposed to the fluid in said reservoir, and wherein said driver acts upon the fluid in said reservoir.

16. The system of claim 14 wherein the walls of said delivery system are not receptive to the target.

17. A method, comprising:
    exposing a sensor of the type having a substrate carrying a sealed micromachined mesh membrane to a substance to be analyzed, a recognition group attached to said membrane, said recognition group being receptive to a target;
    actuating said membrane;
    detecting motion of said membrane; and
    analyzing said detected motion to determine if the target was found in said substance to be analyzed.

18. The method of claim 17 wherein said actuating includes direct actuation by a resonating element in contact with said sealed micromachined mesh membrane.

19. The method of claim 17 wherein said actuating includes indirect actuation by a resonating element in indirect contact with said sealed micromachined mesh membrane.

20. The method of claim 17 wherein said analyzing includes determining one of changes in resonant frequency of the membrane, changes in amplitude decay rates, the appearance of higher order harmonic vibrations, and the disappearance of higher order harmonic vibrations.

21. A sensor, comprising:
    a substrate;
    a sealed micromachined mesh membrane carried by said substrate;
    a recognition group attached to said membrane, said recognition group being receptive to a target;
    a driver for actuating said membrane; and
    a detector for detecting motion of said membrane.

22. The sensor of claim 21 wherein said membrane has a plurality of recognition groups, each of said plurality of recognition groups being receptive to a target.

23. The sensor of claim 22 wherein certain of said plurality of recognition groups are responsive to different targets.

24. The sensor of claim 22 wherein the area occupied by certain of said plurality of recognition groups have one of different areal densities and different sizes.

25. The sensor of claim 22 wherein the area occupied by certain of said plurality of recognition groups have different positions and different shapes.

26. The sensor of claim 21 additionally comprising a layer of gold covering at least a portion of said membrane, wherein said layer of gold enables the attaching of said recognition group to said membrane.

27. The sensor of claim 21 wherein said driver includes one of an electrostatic driver and a resonating element in contact with said membrane.

28. The sensor of claim 21 wherein said detector includes one of a capacitive, piezoresistive, piezoelectric, and optical detector.

29. The sensor of claim 21 additionally comprising analyzing circuitry responsive to said detector.

30. The sensor of claim 21 additionally comprising resistors positioned to heat at least a portion of said membrane.

* * * * *